United States Patent
Hirano et al.

[11] Patent Number: 6,020,514
[45] Date of Patent: Feb. 1, 2000

[54] PROCESS FOR PRODUCING DI-TERT-BUTYL DICARBONATE

[75] Inventors: Naoki Hirano; Fumiaki Iwasaki, both of Tokuyama, Japan

[73] Assignee: Tokuyama Corporation, Yamaguchi, Japan

[21] Appl. No.: 09/185,542

[22] Filed: Nov. 4, 1998

[30]     Foreign Application Priority Data

Nov. 10, 1997  [JP]  Japan ................................ 9-307368

[51] Int. Cl.⁷ ............................ C07C 68/06; C07C 68/04
[52] U.S. Cl. .............................................................. 558/276
[58] Field of Search ............................................. 558/276

[56]              References Cited

U.S. PATENT DOCUMENTS 5,151,542  9/1992  Kurimoto et al. .
5,750,758  5/1998  Zambounis et al. ................. 558/276

FOREIGN PATENT DOCUMENTS 247846  12/1987  Czechoslovakia .
256559   2/1988  European Pat. Off. .
0764682  3/1997  European Pat. Off. .
63-51358  4/1988  Japan .
4103562   4/1992  Japan .
4217643   8/1992  Japan .
6-145112  5/1994  Japan .

OTHER PUBLICATIONS

Database WPI, Week 9351, Derwent Publications Ltd., London, GB; JP 05 310648 A (Tokuyama Soda KK), Nov. 22, 1993.

Joseph H. Howe et al: "An Improved Synthesis of Dicarbonates: Di–t–butyl Dicarbonate" Journal of Organic Chemistry, vol. 27, No. 5, May 11, 1962, pp 1901–1902.

Borovicka, Milos et al. Czechoslovak Patent CS 247846, Jan. 15, 1987; STN® CAPlus database, Accession No. 1988:408418, 1988.

Miyazaki, Kojiro et al. Japan Kokai Tokkyo Koho JP 04–103,562, Apr. 6, 1992; STN® CAPlus database, Accession No. 1992:511135, 1992.

Iwasaki, Fumiaki et al. Japan Kokai Tokkyo Koho JP 06–145112, May 24, 1994; STN® CAPlus database, Accesision No. 1994;630348, 1994.

*Primary Examiner*—Michael G. Ambrose

[57]                ABSTRACT

A process for producing di-tert-butyl dicarbonate by continuously carrying out the following steps of reacting tert-butyl alcohol with sodium to form sodium tert-butoxide, reacting the sodium tert-butoxide with carbon dioxide to form mono-tert-butyl sodium carbonate, and reacting the mono-tert-butyl sodium carbonate with an aromatic sulfonyl halide such as p-toluenesulfonyl chloride in the presence of a tertiary amine such as N,N,N',N'-tetramethylethylenediamine, without isolating an intermediate in the middle of each reaction stage. This process is an industrially advantageous process for producing di-tert-butyl dicarbonate from tert-butyl alcohol and an alkali metal.

14 Claims, No Drawings

PROCESS FOR PRODUCING DI-TERT-BUTYL DICARBONATE

FIELD OF THE INVENTION

The present invention relates to a process for producing di-tert-butyl dicarbonate from tert-butyl alcohol and an alkali metal as starting materials by carrying out reaction steps continuously. More specifically, it relates to a novel process for producing di-tert-butyl dicarbonate through a series of steps by using tert-butyl alcohol not only as a reaction product but also as a solvent until the final step, without isolating an intermediate in each step.

DESCRIPTION OF THE PRIOR ART

Di-tert-butyl dicarbonate is an important compound as an agent for protecting an amino group in the synthesis of pharmaceuticals and agricultural chemicals.

Conventionally known methods for synthesizing di-tert-butyl dicarbonate include one that comprises dissolving an alkali metal tert-butoxide in a solvent such as a hydrocarbon, introducing carbon dioxide to be reacted with the solution to convert it into a mono-tert-butyl alkali metal carbonate, and reacting this compound with an aromatic sulfonyl halide in the presence of a tertiary amine (refer to JP-A 4-103562) (the term "JP-A" as used herein means an "unexamined published Japanese patent application"); one that comprises reacting a mono-tert-butyl alkali metal carbonate produced in the same manner as described above with methanesulfonyl chloride in the presence of a phase transfer catalyst and/or an aromatic amine (refer to JP-A 4-217643); one that comprises reacting a mono-tert-butyl alkali metal carbonate produced in the same manner as described above with phosgene in the presence of a tertiary amine (refer to JP-A 63-51358); and the like.

In all of the above methods, an alkali metal tert-butoxide must be used as a starting material. An alkali metal tert-butoxide is available on the market as a reagent. Although an alkali metal tert-butoxide is generally produced by a reaction between an excess of tert-butyl alcohol and an alkali metal, the obtained alkali metal tert-butoxide forms a complex with the tert-butyl alcohol. Therefore, the alkali metal tert-butoxide cannot be isolated only by distilling off the excess of the tert-butyl alcohol under heat from the reaction mixture to concentrate the reaction mixture. A complicated operation such as purification by sublimation under the conditions of a high temperature and a high vacuum, or azeotropic distillation by adding an inert solvent is required to remove the tert-butyl alcohol after the concentration. Furthermore, careful attention must be paid to the handling of the alkali metal tert-butoxide because it is moisture-absorptive and readily decomposes into tert-butyl alcohol and an alkali metal hydroxide. Therefore, it is not easy to use the alkali metal tert-butoxide as an industrial raw material.

In the method disclosed by Czechoslovakian Patent No. 247846, a reaction for obtaining di-tert-butyl dicarbonate is carried out without isolating sodium tert-butoxide obtained from tert-butyl alcohol and sodium. The method, however, involves such a problem that a reaction between mono-tert-butyl sodium carbonate and p-toluenesulfonyl halide takes 20 hours because the reaction is carried out in the absence of a catalyst and in a solvent prepared by mixing large amounts of toluene and N,N-dimethylformamide together.

SUMMARY OF THE INVENTION

It is therefore an object of the present invention to provide a simple process for producing di-tert-butyl carbonate from an alkali metal and tert-butyl alcohol at a high yield.

It is another object of the present invention to provide an industrially advantageous process for producing di-tert-butyl carbonate at a high yield through a series of reactions without isolating an intermediate in the middle of each reaction step.

It is still another object of the present invention to provide a process for producing di-tert-butyl dicarbonate at a high yield in a short period of time.

Other object and advantages of the present invention will become apparent from the following description.

DETAILED DESCRIPTION OF THE PREFERRED EMBODIMENTS

According to the present invention, the above objects of the present invention can be attained by a process for producing di-tert-butyl dicarbonate, which comprises:

(A) the step of reacting an alkali metal with tert-butyl alcohol in an amount of at least 5 moles of the tert-butyl alcohol, based on one mole of the alkali metal to form an alkali metal tert-butoxide;

(B) the step of introducing carbon dioxide into the reaction mixture obtained in the step (A), without isolating the alkali metal tert-butoxide from the reaction mixture to form a mono-tert-butyl alkali metal carbonate; and (C) the step of mixing and reacting an aromatic sulfonyl halide and a tertiary amine with the reaction mixture obtained in the step (B), without isolating the mono-tert-butyl alkali metal carbonate from the reaction mixture, to form di-tert-butyl dicarbonate.

The present invention further provides a process for recycling the tert-butyl alcohol that has served as a reaction solvent in each stage as a feed material and solvent in the step (A) after recovering it.

The process for producing di-tert-butyl dicarbonate of the present invention consists of three synthesis reaction steps. The reaction in the step (A) is for forming an alkali metal tert-butoxide from an alkali metal and tert-butyl alcohol.

Although the alkali metal used is not particularly limited, sodium and potassium are preferred, and sodium, which is easily obtained at a low cost, is advantageously used.

Although these alkali metals are not limited to a particular shape, they are preferably flaky or granular to enhance its reactivity. A state of alkali metal granules with a diameter of 1 to 1,000 μm being dispersed in a medium is particularly preferred.

The required molar amount of the tert-butyl alcohol may be equal to or more than the molar amount of the alkali metal to carry out a reaction therebetween. However, as the tert-butyl alcohol is also used as a solvent, if the amount of the tert-butyl alcohol is too small, agglomeration or coagulation occurs, thereby making stirring or the like difficult to carry out. To avoid this problem, the tert-butyl alcohol is used in an amount of at least 5 moles, based on 1 mole of the alkali metal. On the other hand, if the amount is too large, the procedure of recovering the solvent after the reaction becomes complicated and an apparatus used for this purpose becomes large uneconomically. Therefore, the tert-butyl alcohol is preferably used in an amount of 5 to 50 moles, more preferably 7 to 30 moles, based on 1 mole of the alkali metal.

The reaction temperature in the step (A) is not particularly limited. However, the reaction rate becomes low if the reaction temperature is too low. Therefore, the reaction temperature is preferably 20° C. or higher. The upper limit of the reaction temperature can be as high as the boiling temperature of the tert-butyl alcohol, but it is generally 20 to 200° C., preferably 50 to 160° C. as the reaction can also be carried out under pressure. The reaction time is preferably long enough to carry out the reaction until the alkali metal used is completely reacted. The reaction time is not always constant because it is affected by the shape of the alkali metal or the reaction temperature. It is preferably about 0.1 to 30 hours.

After the completion of the step (A), the reaction mixture obtained in the step (A) is used in the subsequent step (B) without isolating the alkali metal tert-butoxide formed in the step (A). Therefore, after the completion of the step (A), the step (B) can be carried out using the reactor used in the step (A) as it is, or the step (B) can be carried out after the reaction mixture is transferred to another reactor. At the time of carrying out the step (B), the addition of the solvent or the like may be carried out.

The method of reacting the alkali metal tert-butoxide with carbon dioxide in the step (B) is not particularly limited. It may be one in which carbon dioxide is blown into a reaction solution, one in which the reaction is carried out in a carbon dioxide atmosphere, or one in which the reaction is carried out under the pressure of carbon dioxide, for example. When the reaction is carried out under the pressure of carbon dioxide, the pressure of carbon dioxide may be kept at a partial or total pressure of 0.01 kg/cm$^2$ or more, preferably 0.01 to 40 kg/cm$^2$, more preferably 0.1 to 20 kg/cm$^2$.

The reaction temperature in the step (B) is not particularly limited. However, the reaction rate becomes low if the reaction temperature is too low, while the product decomposes if the reaction temperature is too high. Therefore, the reaction temperature is generally 0 to 200° C., preferably 20 to 150° C. Although the reaction time is not always constant because it is affected by the method of reacting the alkali metal tert-butoxide with carbon dioxide or the reaction temperature, it is generally 0.1 to 30 hours. The reaction end point can be generally determined, for example, by measuring the consumption of carbon dioxide.

After the completion of the step (B), the reaction mixture obtained in the step (B) is used in the subsequent step (C) without isolating the mono-tert butyl carbonate alkali metal salt formed in the step (B). Therefore, after the completion of the step (B), the step (C) can be carried out directly or after the reaction mixture obtained in the step (B) is transferred to another reactor.

In the step (C), it is necessary to select an aromatic sulfonyl halide from various sulfonyl halide compounds. In the present invention, when another conventionally known sulfonyl halide, for example, an aliphatic sulfonyl halide such as methanesulfonyl chloride, is used, the yield of di-tert-butyl dicarbonate is greatly reduced. Therefore, it is not suitable for use.

As the aromatic sulfonyl halide used in the step (C) may be used known compounds in which a halogenosulfonyl group is bonded to an aromatic ring without any restrictions. Illustrative examples of the aromatic sulfonyl halide that can be advantageously used in the present invention include benzenesulfonyl chloride, p-toluenesulfonyl chloride, p-ethylbenzenesulfonyl chloride, 2,4-dimethylbenzenesulfonyl chloride, p-chlorobenzenesulfonyl chloride, p-bromobenzenesulfonyl chloride, p-nitrobenzenesulfonyl chloride, 2,4-dichlorobenzenesulfonyl chloride, benzenesulfonyl bromide, p-toluenesulfonyl bromide, p-chlorobenzenesulfonyl bromide, benzenesulfonyl iodide and the like. Of these, benzenesulfonyl chloride and p-toluenesulfonyl chloride are preferred from an economical point of view.

In general, the amount of the aromatic sulfonyl halide used is preferably in the range of 0.3 to 0.5 mole, based on 1 mole of the alkali metal used in the step (A) because 1 mole of di-tert-butyl dicarbonate is produced from 2 moles of the mono-tert-butyl alkali metal carbonate. When the aromatic sulfonyl halide is used in an amount more than 0.5 mole, the possibility that a side reaction takes place tends to increase.

As the tertiary amine used in the step (C), ordinary tertiary amines can be used without any restrictions. Illustrative examples of the tertiary amine include aliphatic tertiary amines such as trimethylamine, triethylamine, N,N,N',N'-tetramethylethylenediamine, N,N,N',N'-tetraethylethylenediamine, N,N,N',N'-tetramethyl-1,3-propanediamine, N,N,N',N'-tetramethyl-1,4-butanediamine, N,N,N',N'-tetramethyl-1,6-hexanediamine, N,N,N',N'-tetraethyl-1,3-propanediamine, N,N,N',N'-tetraethyl-1,4-butanediamine, N,N,N',N'-tetraethyl-1,6-hexanediamine, bis-[2-(N,N-dimethylamino)ethyl]ether, bis-[2-(N,N-dimethylamino)propyl]ether, bis-[2-(N,N-dimethylamino) ethyl]sulfide, bis-[2-(N,N-dimethylamino)propyl]sulfide, 2-(N,N-dimethylamino)ethylethyl ether, 2-(N,N-dimethylamino)ethylethyl sulfide, bis-[2-(N,N-dimethylamino)ethyl]methylamine and 2-dimethylaminoethanol; alicyclic tertiary amines such as 1,4-dimethylpiperazine, 1,4-diazabicyclo[2.2.2]octane, N-methylmorpholine and N-ethylmorpholine; heterocyclic tertiary amines such as pyridine, 4-chloropyridine, 4-bromopyridine, 4-hydroxypyridine, 4-N,N-dimethylaminopyridine and 4-pyrrolidinopyridine; and aromatic tertiary amines such as N,N-dimethylbenzylamine, N,N-diethylbenzylamine and N,N-dimethylaniline; and the like.

Of these, N,N,N',N'-tetramethylethylenediamine, N,N,N',N'-tetraethylethylenediamine, N,N,N',N'-tetramethyl-1,3-propanediamine, N,N,N',N'-tetramethyl-1,6-hexanediamine, N,N,N',N'-tetraethyl-1,3-propanediamine, N,N,N',N'-tetraethyl-1,6-hexanediamine, N,N,N',N'-tetramethyl-1,4-butanediamine, N,N,N',N'-tetraethyl-1,4-butanediamine, 2-dimethylaminoethanol, pyridine, N,N-dimethylbenzylamine, N,N-diethylbenzylamine, 1,4-dimethylpiperazine, 1,4-diazabicyclo[2.2.2]octane and N-methylmorpholine are preferably used, when the high yield of the target product is taken into consideration.

The amount of the above tertiary amine used is not particularly limited but is preferably in the range of 0.0001 to 0.2 mole, more preferably 0.001 to 0.1 mole, based on 1 mole of the alkali metal used in the step (A) in order to obtain a sufficient reaction rate.

The reaction temperature in the step (C) is not particularly limited. However, the reaction rate becomes low if the reaction temperature is too low, while the product decomposes if the reaction temperature is too high. Therefore, the reaction temperature is generally 0 to 100° C., preferably 20 to 80° C. The reaction time is not always constant because it is affected by the amount of the tertiary amine or the reaction temperature, but it is generally 0.1 to 30 hours.

The step (C) can be carried out at atmospheric pressure, an increased pressure or a reduced pressure. To suppress the decomposition of the mono-tert-butyl alkali metal carbonate, the step (C) is preferably carried out at atmospheric pressure or in a carbon dioxide atmosphere or under the pressure of carbon dioxide. When the step (C) is carried out under the pressure of carbon dioxide, the partial or total pressure of carbon dioxide is preferably 0.01 to 40 kg/cm$^2$, more preferably 0.1 to 20 kg/cm$^2$.

In the present invention, other inert solvent can be used in addition to the tert-butyl alcohol in each reaction step. In this case, taking the reaction rate and the yield of the target product into consideration, the amount of the other inert solvent is preferably 0.1 part by volume or less, more preferably 0.05 part by volume or less, based on 1 part by volume of the tert-butyl alcohol. It is substantially preferred the most to use only tert-butyl alcohol as a solvent.

The kind of the other inert solvent used is not particularly limited. Illustrative examples of the solvent include aromatic hydrocarbons such as benzene, toluene and xylene; aliphatic hydrocarbons such as hexane and heptane; aliphatic hydrocarbon halides such as dichloromethane and carbon tetrachloride; ethers such as 1,4-dioxane and tetrahydrofuran; nitrites such as acetonitrile and propionitrile; amides such as N,N-dimethylformamide, N,N-dimethylacetamide and N-methylpyrrolidone; dimethyl sulfoxide; and the like.

As the method of isolating and purifying the di-tert-butyl dicarbonate formed in the step (C) may be used conventional methods without any restrictions. For example, the di-tert-butyl dicarbonate can be isolated and purified by distilling off the solvent after the completion of a reaction, adding water, extracting the di-tert-butyl carbonate with an organic solvent incompatible with water and distilling off the solvent from the organic layer.

The di-tert-butyl carbonate obtained by this procedure can be used, for example, in a reaction for protecting the amino group of a desired compound as it is, or after it is decolorized and purified by distillation or the like according to circumstances, as a matter of course.

Meanwhile, the solvent separated by distillation, particularly the tert-butyl alcohol can be reused in the step (A) as it is or after purified.

The present invention makes it possible to produce di-tert butyl dicarbonate from tert-butyl alcohol and an alkali metal by carrying out the three steps (A) to (C) continuously, using the tert-butyl alcohol which is one of the feed materials for forming an alkali metal tert-butoxide as a solvent and an aromatic sulfonyl halide as a sulfonyl halide compound, without carrying out the complicated operation of isolating an intermediate such as an alkali metal tert-butoxide or the like in the middle of each reaction step. Therefore, the present invention provides an industrially advantageous process.

The following examples are given to further illustrate the present invention, while it is in no way limited thereto.

EXAMPLE 1

232.5 Grams (3.14 moles) of tert-butyl alcohol and 7.8 g (0.339 mole) of flaky sodium were charged into a 1,000 ml glass autoclave equipped with a stirrer, thermometer, pressure gauge and gas introduction tube and were reacted with each other at 83° C. for 6 hours (step (A)). After the solid sodium disappeared, carbon dioxide was injected, and a reaction was carried out at 80° C. for 3 hours at the pressure of 5 kg/cm$^2$, which consists of a partial pressure of carbon dioxide of 4 kg/cm$^2$ and a partial pressure of air of 1 kg/cm$^2$ (step (B)). After cooling, 29.08 g (0.1525 mole) of p-toluenesulfonyl chloride and 0.39 g (3.39×10$^{-3}$ mole) of N,N,N',N'-tetramethylethylenediamine were added, and a reaction was carried out at 30° C. for 3 hours at the pressure of 3 kg/cm$^2$, which consists of a partial pressure of carbon dioxide of 2 kg/cm$^2$ and a partial pressure of air of 1 kg/cm$^2$ (step (C)). After the reaction, the tert-butyl alcohol as a solvent was recovered by distillation, 300 ml of water was added to the residue to dissolve the residual salt, and di-tert-butyl dicarbonate was extracted with 250 ml of toluene. Thereafter, the organic layer was washed twice with 150 ml of water, and the organic solvent was distilled off to give 27.86 g of di-tert-butyl dicarbonate. The yield was 83.7% based on p-toluenesulfonyl chloride. The recovered tert-butyl alcohol was used as a feed material and a solvent in the step (A).

EXAMPLES 2 to 9

The procedure of Example 1 was repeated except that the aromatic sulfonyl halide, the tertiary amine and the reaction time of the step (C) were changed as shown in Table 1. The results are shown in Table 1.

TABLE 1

| Example | aromatic sulfonyl halide (0.1525 mole) | tertiary amine (0.339 × 10$^{-3}$ mole) | reaction time (hr) | yield (%) |
|---|---|---|---|---|
| 2 | p-toluenesulfonyl chloride | 1,4-dimethylpiperazine | 3 | 82.8 |
| 3 | p-toluenesulfonyl chloride | pyridine | 10 | 75.4 |
| 4 | p-toluenesulfonyl chloride | N,N-dimethylbenzylamine | 5 | 76.8 |
| 5 | p-toluenesulfonyl chloride | N-methylmorpholine | 10 | 72.6 |
| 6 | p-toluenesulfonyl chloride | N,N,N',N'-tetramethyl-1,3-propanediamine | 3 | 83.2 |
| 7 | benzenesulfonyl chloride | N,N,N',N'-tetramethylethylenediamine | 4 | 81.2 |
| 8 | benzenesulfonyl chloride | 1,4-dimethyipiperazine | 4 | 80.3 |
| 9 | benzenesulfonyl chloride | N,N-dimethylbenzylamine | 6 | 74.5 |

EXAMPLES 10 and 11

The procedure of Example 1 was repeated except that the amount of the tert-butyl alcohol was changed as shown in Table 2. The results are shown in Table 2.

TABLE 2

| Example | amount of tert-butyl alcohol (g) | yield (%) |
|---|---|---|
| 10 | 348.5 | 80.8 |
| 11 | 465.0 | 76.6 |

EXAMPLE 12

The procedure of Example 1 was repeated except that a reaction was carried out at 30° C. for 8 hours in the step (B). As a result, 27.06 g of di-tert-butyl dicarbonate was obtained. The yield was 81.3% based on p-toluenesulfonyl chloride.

EXAMPLES 13 to 17

The procedure of Example 1 was repeated except that a reaction was carried out at a carbon dioxide partial pressure of 1 kg/cm$^2$ in the step (B) and that the aromatic sulfonyl halide, the tertiary amine, and the reaction temperature and the reaction time of the step (C) were changed as shown in Table 3. The results are shown in Table 3.

TABLE 3

| Example | aromatic sulfonyl halide (0.1525 mole) | tertiary amine (0.339 × 10⁻³ mole) | reaction temperature (° C.) | reaction time (hr) | yield (%) |
| --- | --- | --- | --- | --- | --- |
| 13 | p-toluenesulfonyl chloride | N,N,N',N'-tetramethylethylenediamine | 30 | 3 | 84.5 |
| 14 | p-toluenesulfonyl chloride | N,N,N',N'-tetramethyl-1,6-hexanediamine | 30 | 2 | 79.6 |
| 15 | p-toluenesulfonyl chloride | N,N,N',N'-tetramethylethylenediamine | 50 | 2 | 71.1 |
| 16 | benzenesulfonyl chloride | N,N,N',N'-tetramethylethylenediamine | 30 | 2 | 84.5 |
| 17 | benzenesulfonyl chloride | N,N,N',N'-tetramethyl-1,3-propanediamine | 30 | 2 | 82.3 |

EXAMPLE 18

The procedure of Example 13 was repeated except that the separated and recovered tert-butyl alcohol was used. As a result, 27.32 g of di-tert-butyl dicarbonate was obtained. The yield was 82.1% based on p-toluenesulfonyl chloride.

Comparative Example 1

155 Grams (2.091 moles) of tert-butyl alcohol and 13.0 g (0.5652 mole) of flaky sodium were charged into a 1,000-ml glass autoclave equipped with a stirrer, thermometer, pressure gauge and gas introduction tube and were reacted with each other at 83° C. for 6 hours. After the reaction, it was difficult to stir due to the agglomeration of the formed sodium tert-butoxide. Thereafter, 200 ml of toluene was added, carbon dioxide was injected, and a reaction was carried out at 80° C. for 3 hours at the pressure of 2 kg/cm², which consists of a partial pressure of carbon dioxide of 1 kg/cm² and a partial pressure of air of 1 kg/cm². After cooling, 48.51 g (0.2544 mole) of p-toluenesulfonyl chloride and 0.66 g (5.68×10⁻³ mole) of N,N,N',N'-tetramethylethylenediamine were added, and a reaction was carried out at 30° C. for 10 hours at the pressure of 3 kg/cm², which consists of a partial pressure of carbon dioxide of 2 kg/cm² and a partial pressure of air of 1 kg/cm². After the reaction, 300 ml of water was added to the residue to dissolve the undissolved salt, the organic layer was washed twice with 200 ml of water, and the organic solvent was distilled off to give 31.31 g of di-tert-butyl dicarbonate. The yield was 56.4% based on p-toluenesulfonyl chloride.

What is claimed is:

1. A process for producing di-tert-butyl dicarbonate, which comprises:
   (A) the step of reacting an alkali metal with tert-butyl alcohol in an amount of at least 5 moles of the tert-butyl alcohol, based on one mole of the alkali metal to form an alkali metal tert-butoxide;
   (B) the step of introducing carbon dioxide into the reaction mixture obtained in the step (A), without isolating the alkali metal tert-butoxide from the reaction mixture to form a mono-tert-butyl alkali metal carbonate; and
   (C) the step of mixing and reacting an aromatic sulfonyl halide and a tertiary amine with the reaction mixture obtained in the step (B), without isolating the mono-tert-butyl alkali metal carbonate from the reaction mixture, to form di-tert-butyl dicarbonate,
   wherein the solvent of each reaction step is
   (I) a mixture of tert-butyl alcohol and an inert solvent other than the tert-butyl alcohol, and the other inert solvent is used in an amount of 0.1 part by volume or less, based on 1 part by volume of the tert-butyl alcohol, or
   (II) only tert-butyl alcohol.

2. The process of claim 1, wherein the tert-butyl alcohol is separated and recovered from the reaction mixture of the step (C) and reused in the step (A).

3. The process of claim 1, wherein the tert-butyl alcohol is used in an amount of 5 to 50 moles, based on one mole of the alkali metal.

4. The process of claim 1, wherein the alkali metal is flaky or granular.

5. The process of claim 1, wherein the reaction in the step (B) is carried out under the pressure of carbon dioxide at a partial or total pressure of 0.01 to 40 kg/cm².

6. The process of claim 1, wherein the aromatic sulfonyl halide is benzenesulfonyl chloride or p-toluenesulfonyl chloride.

7. The process of claim 1, wherein the tertiary amine is at least one selected from the group consisting of N,N,N',N'-tetramethylethylenediamine, N,N,N',N'-tetramethyl-1,3-propanediamine, N,N,N',N'-tetramethyl-1,6-hexanediamine, N,N,N',N'-tetraethylethylenediamine, N,N,N',N'-tetraethyl-1,3-propanediamine, N,N,N',N'-tetraethyl-1,6-hexanediamine, N,N,N',N'-tetramethyl-1,4-butanediamine, N,N,N',N'-tetraethyl-1,4-butanediamine, 2-dimethylaminoethanol, pyridine, N,N-dimethylbenzylamine, N,N-diethylbenzylamine, 1,4-dimethylpiperazine, 1,4-diazabicyclo[2.2.2]octane and N-methylmorpholine.

8. The process of claim 1, wherein the reaction in the step (C) is carried out under the pressure of carbon dioxide at a partial or total pressure of 0.01 to 40 kg/cm².

9. The process of claim 1, wherein the solvent of each reaction step is a mixture of tert-butyl alcohol and inert solvent other than the tert-butyl alcohol, and the other inert solvent is used in an amount of 0.1 part by volume or less, based on 1 part by volume of the tert-butyl alcohol.

10. The process of claim 1, wherein only tert-butyl alcohol is substantially used as a solvent in each reaction step.

11. A process for producing di-tert-butyl dicarbonate, which comprises:
   (A) the step of reacting an alkali metal with tert-butyl alcohol in an amount of 5 to 50 moles of the tert-butyl alcohol, based on one mole of the alkali metal to form an alkali metal tert butoxide;
   (B) the step of introducing carbon dioxide into the reaction mixture obtained in the step (A), without isolating the alkali metal tert-butoxide from the reaction mixture to form a mono-tert-butyl alkali metal carbonate; and (C) the step of mixing and reacting an aromatic sulfonyl halide and a tertiary amine with the reaction mixture obtained in the step (B), without isolating the mono-tert-butyl alkali metal carbonate from the reaction mixture, to form di-tert-butyl dicarbonate, wherein the solvent of each reaction step consists essentially of the tert-butyl alcohol.

12. The process of claim 11, wherein the step (C) is carried out in about 3 hours and the yield of di-tert-butyl dicarbonate is about 71% or more.

13. The process of claim 11, wherein the tert-butyl alcohol is used in an amount of 7 to 30 moles, based on one mole of the alkali metal.

14. The process of claim 11, wherein the solvent of each reaction step is a mixture of tert-butyl alcohol and an inert solvent other than the tert-butyl alcohol, and the other inert solvent is used in an amount of 0.1 part by volume or less, based on 1 part by volume of the tert-butyl alcohol.

* * * * *